(12) United States Patent
Berthier et al.

(10) Patent No.: US 9,283,559 B2
(45) Date of Patent: Mar. 15, 2016

(54) LID FOR FUNCTIONALIZED MICROFLUIDIC PLATFORM AND METHOD

(75) Inventors: Erwin Berthier, Madison, WI (US); Peter Cavnar, Madison, WI (US); David John Guckenberger, Oconomowoc, WI (US); David Beebe, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 323 days.

(21) Appl. No.: 13/467,584

(22) Filed: May 9, 2012

(65) Prior Publication Data

US 2013/0302842 A1 Nov. 14, 2013

(51) Int. Cl.
| | |
|---|---|
| C12M 1/34 | (2006.01) |
| C12M 3/00 | (2006.01) |
| B01L 3/00 | (2006.01) |
| G01N 33/50 | (2006.01) |
| A01N 1/02 | (2006.01) |
| B01L 7/00 | (2006.01) |

(52) U.S. Cl.
CPC ......... *B01L 3/502715* (2013.01); *A01N 1/0263* (2013.01); *A01N 1/0268* (2013.01); *G01N 33/5005* (2013.01); *B01L 7/50* (2013.01); *B01L 2200/027* (2013.01); *B01L 2300/044* (2013.01); *B01L 2300/047* (2013.01); *B01L 2300/0672* (2013.01); *B01L 2300/0816* (2013.01); *B01L 2300/0887* (2013.01); *B01L 2400/0406* (2013.01); *B01L 2400/0481* (2013.01); *B01L 2400/0677* (2013.01); *B01L 2400/0683* (2013.01); *B01L 2400/0694* (2013.01); *B01L 2400/086* (2013.01)

(58) Field of Classification Search
CPC ... A01N 1/0268; B01L 3/502715; B01L 7/50; B01L 7/52; B01L 2200/027; B01L 2300/044; B01L 2300/047; B01L 2300/0672; B01L 2300/0816; B01L 2300/0887; B01L 2400/0406; B01L 2400/0481; B01L 2400/0677; B01L 2400/0694; B01L 2400/086
USPC .......................................... 435/288.5, 287.2
See application file for complete search history.

(56) References Cited

U.S. PATENT DOCUMENTS

| | | | |
|---|---|---|---|
| 2004/0209349 A1* | 10/2004 | Goldman et al. | 435/287.1 |
| 2006/0057629 A1* | 3/2006 | Kim | 435/6 |
| 2006/0205085 A1* | 9/2006 | Handique et al. | 436/177 |
| 2012/0028342 A1* | 2/2012 | Ismagilov et al. | 435/283.1 |

OTHER PUBLICATIONS

"SlipChip", Wenbin Du et al, Lab Chip, 2009, 9, 2286-2292.

* cited by examiner

*Primary Examiner* — Michael Hobbs
(74) *Attorney, Agent, or Firm* — Boyle Fredrickson, S.C.

(57) ABSTRACT

A microfluidic device and method is provided for handheld diagnostics and assays. A first substance is frozen in a cryopreservation fluid in a first well of a lid. The lid includes a first surface communicating with a first port of the first well and a second surface communicating with a second port of the first well. A porous membrane is affixed to the first surface so as to overlap the first port and a non-porous membrane is affixed to the second surface so as to overlap the second port. The first substance may be dialytically freed from the cryopreservation fluid at a user desired time. Thereafter, the lid may be moved from a first position wherein the lid is spaced from a base to a second position wherein the lid is adjacent the channel in the base such that the first substance communicates with the input of the channel.

8 Claims, 6 Drawing Sheets

LID FOR FUNCTIONALIZED MICROFLUIDIC PLATFORM AND METHOD

REFERENCE TO GOVERNMENT GRANT

This invention was made with government support under CA137673 awarded by the National Institutes of Health. The government has certain rights in the invention.

FIELD OF THE INVENTION

This invention relates generally to microfluidic devices, and in particular, to a lid for a functionalized microfluidic platform and method for freezing, storing, shipping, and thawing cell suspensions that maintains their viability and allows for their subsequent culture and study.

BACKGROUND AND SUMMARY OF THE INVENTION

The field of microfluidics has matured significantly over the past two decades. Compelling platforms have been produced to address problems in traditional cell biology techniques that were previously too difficult to solve. Limitations of traditional cell biology techniques have been primarily due to onerous labor requirements and limited spatial and temporal control of the cells' microenvironment. Microfluidics has provided significant efficiency gains by reducing reagent and cell requirements which, in turn, has allowed for high-throughput processing and analysis of a large array of experimental conditions. Microfluidic systems also offer significantly greater control of the cells' microenviroment, such as flow rate, extracellular matrix (ECM) properties, and soluble factor signaling (e.g., forming a chemical gradient in diffusion dominant conditions). However, for microfluidics to make further inroads into cell biology, new microfluidic assays must be cheaper, faster, and in qualitative agreement with techniques traditionally used by biologists. It can be appreciated that microfluidics has tremendous potential to contribute to the development of drug therapies to fight cancer, point-of-care diagnostics for HIV in developing countries, and numerous other applications that are critical to the health and well being of individuals worldwide.

While current microfluidic devices provide a significant improvement in the ability to study fundamental aspects of cell biology, the adoption of microfluidic devices in clinical settings has been slow due to the high level of technicality and external equipment required. For example, current microfluidic assay methods require steps such as washing, flushing, pipetting, and transferring of cells and other materials. As such, most conventional microfluidic devices typically incorporate external elements, such as tubing and syringe pumps, to provide the valving and the mixing functionality necessary to enable an entire assay to be performed within a microfluidic system. These external elements diminish the simplicity and advantages of a microfluidic platform for biological assays.

Further, as is known, the discovery of compounds of interest for therapeutic or research applications is a complex, multitiered process that requires a number of assays of increasing relevance, from biochemical screens and in-vitro live cell assays, to in-vivo animal models. Currently, many laboratories in the areas of natural products purification, microbiology, and toxicology are focused on isolating compounds with putative biological activity for the purpose of discovering new drugs or determining factors of microbial virulence and cytotoxicity. These laboratories have developed low-cost and relatively easy assays to identify compounds of interest through large-scale biochemical screens. In-vitro live-cell assays are an essential step before deciding to pursue costly in-vivo studies, as they: 1) provide more physiologically relevant insight on the biological activity of a compound; 2) are much more time-efficient then prior methodologies; and 3) reduce animal use. However, the accessibility of live-cell assays is limited because they require expensive equipment, a plethora of perishable reagents, and highly trained researchers. These costs and training requirements represent a significant barrier for researchers who are interested in performing an initial in-vitro screening assay. Hence, it is highly desirable to provide a microfluidic platform capable of performing assays, including in-vitro live-cell assays, which do not require any external equipment to operate and which can be adapted to a wide range of situations.

Therefore, it is a primary object and feature of the present invention to provide a functionalized lid for a microfluidic platform and a method for freezing, storing, shipping, and thawing cell suspensions in a manner that maintains their viability and allows their subsequent culture and study.

It is a further object and feature of the present invention to provide a functionalized lid for a microfluidic platform and a method for freezing, storing, shipping, and thawing cell suspensions which do not require any external equipment to operate and which can be adapted to a wide range of situations.

It is a still further object and feature of the present invention to provide a microfluidic platform and a method for freezing, storing, shipping, and thawing cell suspensions which are simple to implement and inexpensive to manufacture.

In accordance with the present invention, a lid is provided for a microfluidic platform. The microfluidic platform includes a base having outer surface and a channel therethough for receiving fluid therein. The channel has input and output ports communicating with the outer surface. The lid includes a body having a first well extending therethrough. The first well includes first and second ports communicating therewith and is adapted for receiving a first substance therein. A first membrane extends over the first port of the lid. The first membrane retains the first substance in the first well and allows a second substance to diffuse therethrough. A non-porous second membrane extends over the second port. The second membrane preventing the second substance form diffusing therethrough.

The body may include first and second spaced surfaces. The first port communicates with the first surface and the second port communicates with the second surface. The first and second surfaces may be planar. The first surface lies in a first plane and the second surface lies in a second plane generally parallel to the first plane. An absorbent may be provided adjacent the second surface and a removable seal may overlap the second membrane for isolating the first substance in the first well. The lid is movable between a first position wherein the lid is spaced from the base to a second position wherein the lid is adjacent the channel such that the first substance communicates with the input of the channel.

In accordance with a further aspect of the present invention, a method is provided for handheld diagnostics and assays. The method includes the step of capturing a first substance in a cryopreservation fluid in a first well of a lid. The lid includes first and second ports communicating with the first well. The first substance is dialytically freeing from the cryopreservation fluid.

In addition, it is contemplated to provide a channel having an input and an output in a base. The lid is moved from a first position wherein the lid is spaced from the base to a second position wherein the lid is adjacent the channel such that the first substance communicates with the input of the channel. A first membrane may be provided over the first port of the lid. The first membrane retains the first substance in the first well and allowing a dialysis fluid to diffuse therethrough. A second membrane may be provided over the second port. The second membrane prevents a dialysis fluid from diffusing therethrough.

A channel having an input and an output in a base may be provided. The lid may be moved from a first position wherein the lid is spaced from the base to a second position wherein the lid is adjacent the channel such that the first substance communicates with the input of the channel. The first substance may be drawn through the channel, e.g. by positioning an absorbent in communication with the output of the channel.

In accordance with a still further aspect of the present invention, a method is provided from for handheld diagnostics and assays. The method includes the step of freezing a first substance in a cryopreservation fluid in a first well of a lid. The lid includes a first surface communicating with a first port of the first well and a second surface communicating with a second port of the first well. A porous membrane is affixed to the first surface so as to overlap the first port and a non-porous membrane is affixed to the second surface so as to overlap the second port. The first substance is dialytically freed from the cryopreservation fluid.

The method may further include the step of providing a channel having an input and an output in a base. The lid may be moved from a first position wherein the lid is spaced from the base to a second position wherein the lid is adjacent the channel such that the first substance communicates with the input of the channel. The first substance may be drawn through the channel, e.g. by positioning an absorbent in communication with the output of the channel. A seal may be removed from the non-porous membrane so as to allow the first substance to pass therethrough. Alternatively, the non-porous membrane may be pierced so as to allow the first substance to pass therethrough.

It is intended for the porous membrane to retain the first substance in the first well and to allow a dialysis fluid to diffuse therethrough. On the other hand, the non-porous membrane prevents the dialysis fluid from diffusing therethrough. The step of dialytically freeing the first substance from the cryopreservation fluid includes the step of depositing the lid in a dialysis fluid for a time period.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings.

DETAILED DESCRIPTION OF THE DRAWINGS

Figure 1:
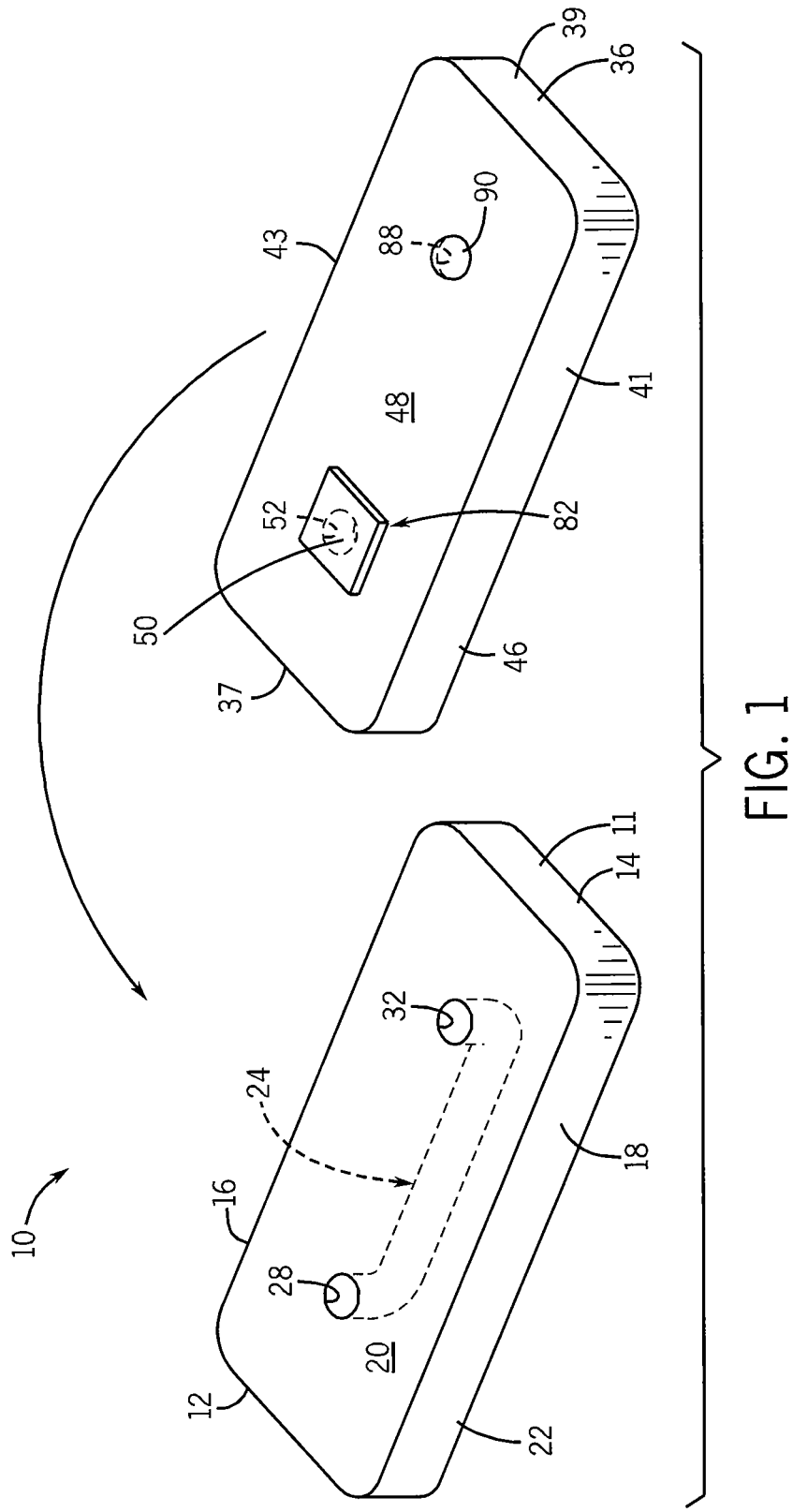
FIG. 1 is an exploded, isometric view of a microfluidic device in accordance with the present invention.

Referring to FIGS. 1-4, a microfluidic device for performing a methodology in accordance with the present invention is generally designated by the reference numeral 10. Microfluidic device 10 may be formed from polystyrene (PS), however, other materials are contemplated as being within the scope of the present invention. In the depicted embodiment, microfluidic device 10 includes base 11 having first and second ends 12 and 14, respectively; first and second sides 16 and 18, respectively; and upper and lower surfaces 20 and 22, respectively. Channel 24 extends through base 11 of microfluidic device 10 and includes a first vertical portion 26 terminating at an input port 28 that communicates with upper surface 20 of base 11 of microfluidic device 10 and a second vertical portion 30 terminating at an output port 32 also communicating with upper surface 20 of base 11 of microfluidic device 10. First and second vertical portions 26 and 30, respectively, of channel 24 are interconnected by and communicate with horizontal portion 34 of channel 24. The dimension of channel 34 connecting input port 28 and output port 32 is arbitrary.

Microfluidic device 10 further includes lid 36 having first and second ends 37 and 39, respectively; first and second sides 41 and 43, respectively; and upper and lower surfaces 46 and 48, respectively. Similar to base 11, lid 36 may be formed from polystyrene (PS), however, other materials are contemplated as being within the scope of the present invention. As best seen in FIGS. 2a-2e, lid 36 further includes first well 50 extending therethrough. First well 50 has a first end terminating at first port 51 that communicates with upper surface 46 and a second end terminating at second port 52 that communicates with lower surface 48. The diameter of second port 52 is generally equal to the diameter of input port 28 in base 11. It can be appreciated that while first and second ports 51 and 52, respectively, are depicted as being on opposites surfaces of lid 36, first and second ports 51 and 52, respectively, may communicate with a single surface or other surfaces of lid 36 without deviating from the scope of the present invention.

Non-porous membrane 82 overlaps second port 52 of first well 50 of lid 36 and is bonded to lower surface 48 thereof. It is contemplated for non-porous membrane 82 to include hole 83 therethrough and for first seal 85 to be removably bonded to outer surface 82a of non-porous membrane 82 and/or lower surface 48 of lid 36, FIG. 2b, to hermetically isolate the interior of first well 50, as hereinafter described. Lid 36 further includes second well 88 formed in lower surface 48 thereof. As hereinafter described, in order to facilitate fluid flow in channel 24, it is contemplated to provide absorbent 90 in second well 88.

Figure 2A:
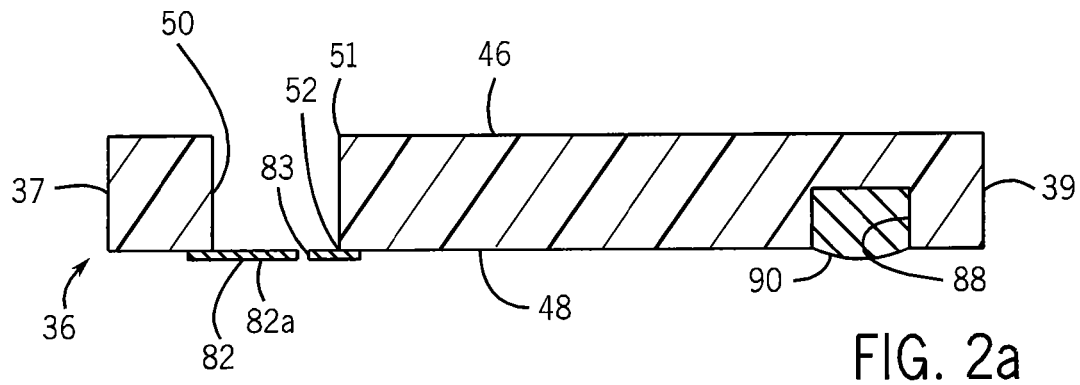
FIG. 2a is a cross sectional view of a lid of the microfluidic device of FIG. 1 in accordance with a first step of the methodology of the present invention.
Figure 2B:
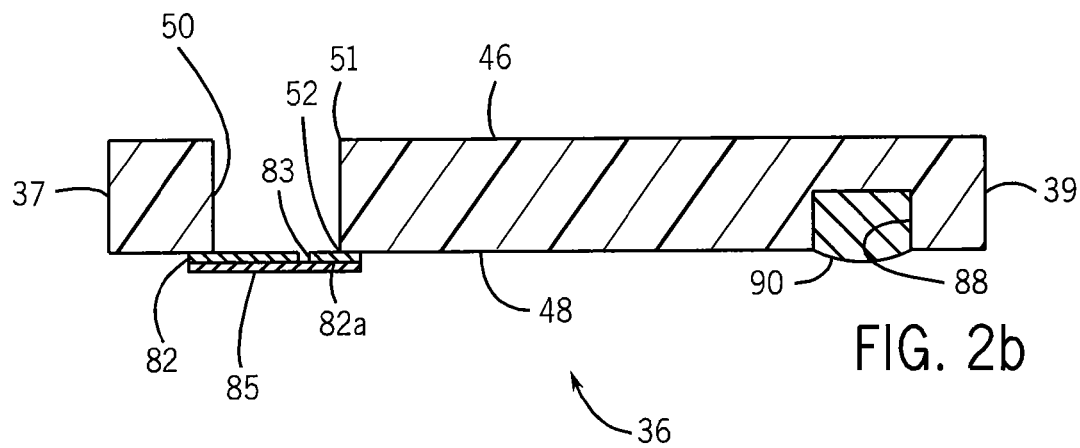
FIG. 2b is a cross sectional view of a lid of FIG. 2a in accordance with a second step of the methodology of the present invention.
Figure 2C:
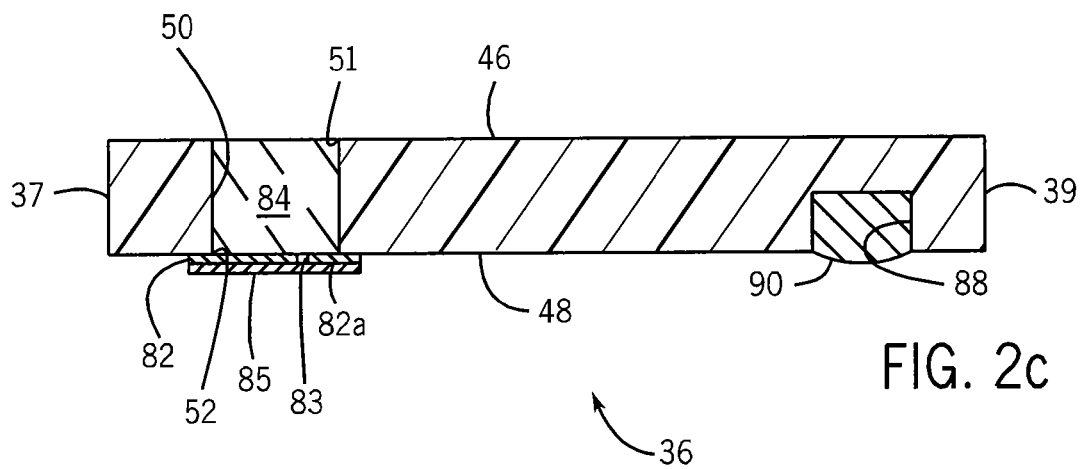
FIG. 2c is a cross sectional view of a lid of FIG. 2b in accordance with a third step of the methodology of the present invention.
Figure 2D:
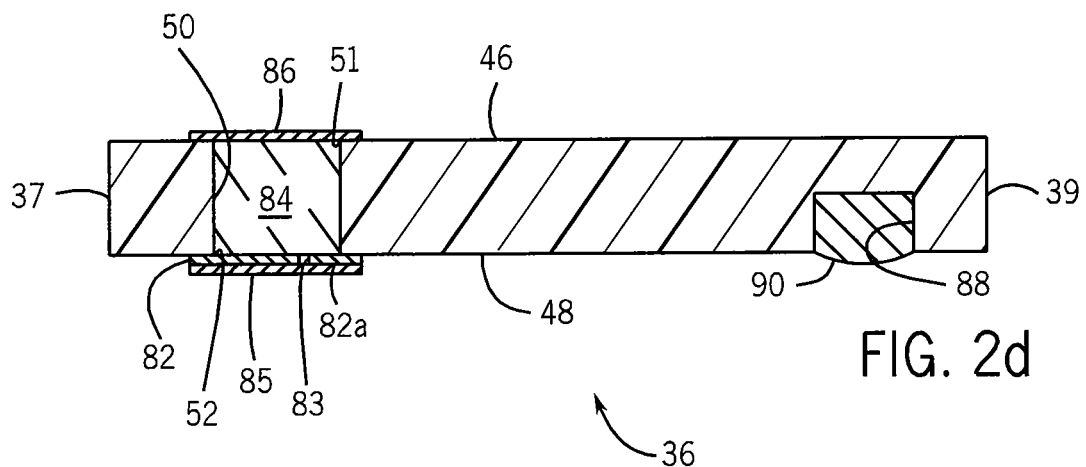
FIG. 2d is a cross sectional view of a lid of FIG. 2c in accordance with a fourth step of the methodology of the present invention.
Figure 2E:
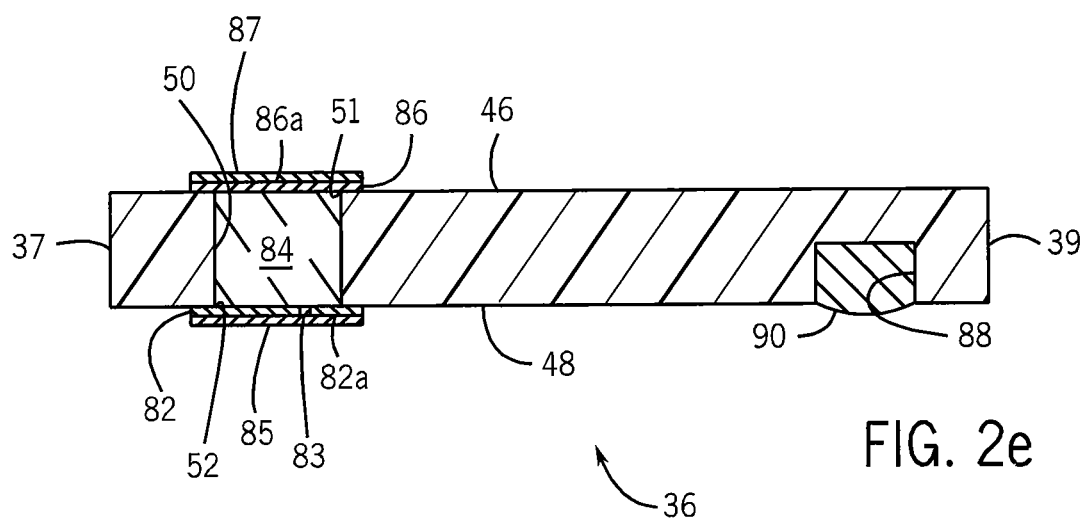
FIG. 2e is a cross sectional view of a lid of FIG. 2d in accordance with a fifth step of the methodology of the present invention.
Figure 3:
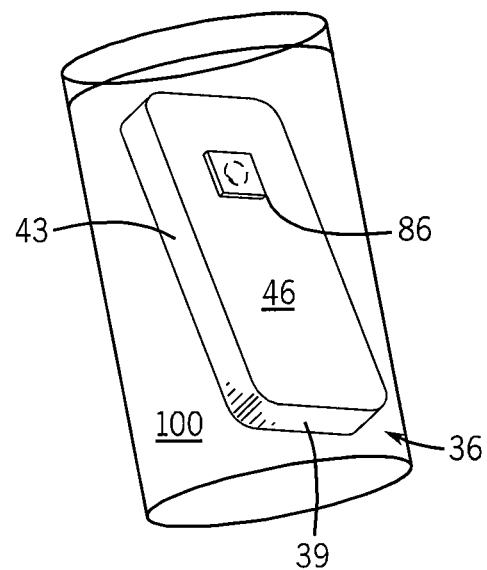
FIG. 3 is an isometric view of a lid of the microfluidic device of FIG. 1 in accordance with a sixth step of the methodology of the present invention.

In operation, it is contemplated to utilize microfluidic device 10 to perform one or a series of steps of a desired assay, FIG. 2c. More specifically, first well 50 of lid 36 is loaded with a desired substance 84, such as cells and reagents, along with a cryopreservation fluid, e.g. dimethyl sulfoxide (DMSO). The cryopreservation fluid is added to substance 84 during the freezing process, hereinafter described, to prevent crystallization and cell death. Porous membrane 86 is bonded to upper surface 48 of lid 36 so as to overlap first port 51, FIG. 2d, and second seal 87 is removably bonded to outer surface 86a of porous membrane 86 and/or upper surface 46 of lid 36 to hermetically isolate the interior of first well 50, FIG. 2e. As described, substance 84 and the cryopreservation fluid in first well 50 is captured between non-porous membrane 82 and porous membrane 86. For reasons hereinafter described, it is intended for porous membrane 86 to includes micropores therein having pore sizes in a desired range, i.e., from 0.1 μm to 3 μm, so as to allow a predetermined fluid to pass therethrough, but retain substance 84 in first well 50. With substance 84 and the cryopreservation fluid captured in first well 50, substance 84 and the cryopreservation fluid may be frozen in accordance with established procedures in first well 50 of lid 36 for better packaging, storage and shipping.

In order to flow substance 84 into channel 24 through base 11 of microfluidic device 10, substance 84 must be freed from the cryopreservation fluid. By way of example, second seal 87 is removed from lid 36 so as to expose porous membrane 86. Thereafter, lid 36 is inserted into a bath of dialysis fluid 100, e.g. cell culture media, for a time period, e.g. two to five minutes, FIG. 3. Dialysis fluid 100 diffuses through porous membrane 86 and frees substance 84 from the cryopreservation fluid. Once substance 84 is freed, as heretofore described, channel 24 is filled with a predetermined fluid and first seal 85 is removed from lid 36 such that hole 83 is exposed. Alternatively, first seal 85 and non-porous membrane 82 may be pieced so as to allow substance 84 to flow therethrough. Lid 36 is then positioned on base 11 such that: 1) lower surface 48 of lid 36 is bought into contact with or adjacent to upper surface 20 of base 11; 2) second port 52 in lid 36 is aligned with and brought into close proximity with input port 28 in base 11 such that substance 84 is in fluid communication with channel 24 through hole 83; and 3) absorbent 90 contacts the fluid in channel 24 at output port 32 such that fluid flow within channel 24 is induced. Alternatively, in order to induce fluid flow in channel 24, absorbent 90 in second well 88 may be removed and an input of a capillary (not shown) may be provided in communication with second well 88. The output of the capillary may operatively connected to a pumping mechanism (not shown).

Figure 4:
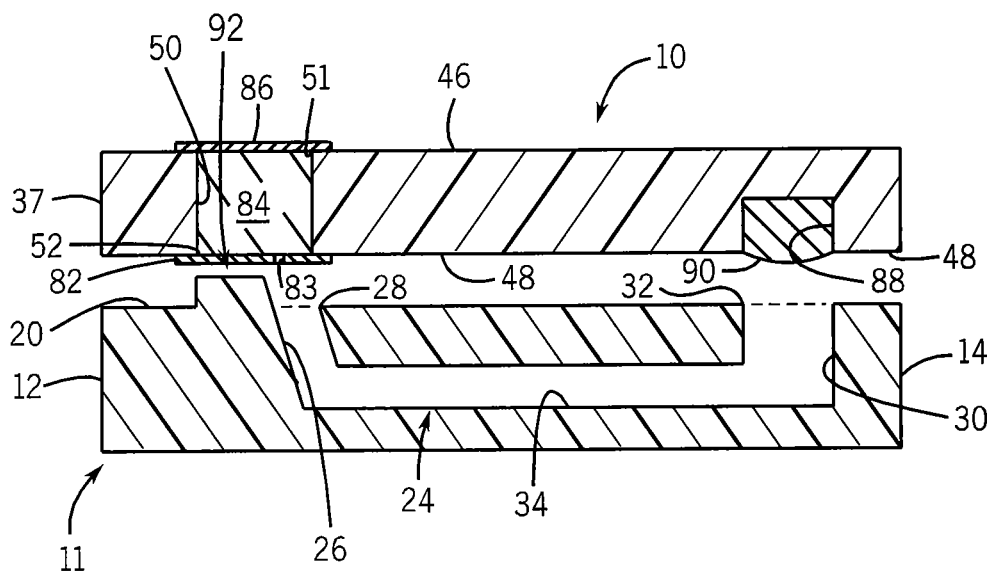
FIG. 4 is an enlarged, cross sectional view showing a microfluidic device for effectuating the methodology of the present invention.
Figure 5:
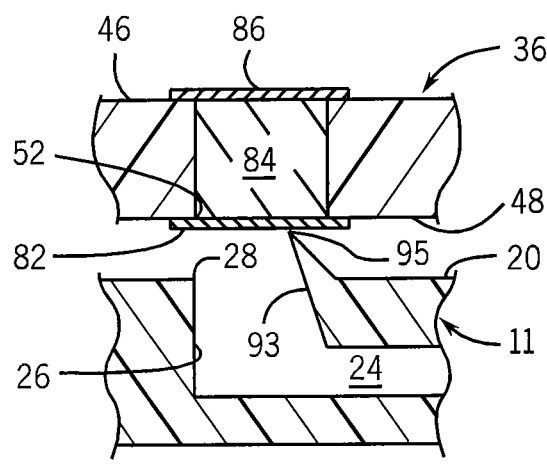
FIG. 5 is an enlarged, cross sectional view showing an alternate embodiment of a microfluidic device for effectuating the methodology of the present invention.
Figure 6:
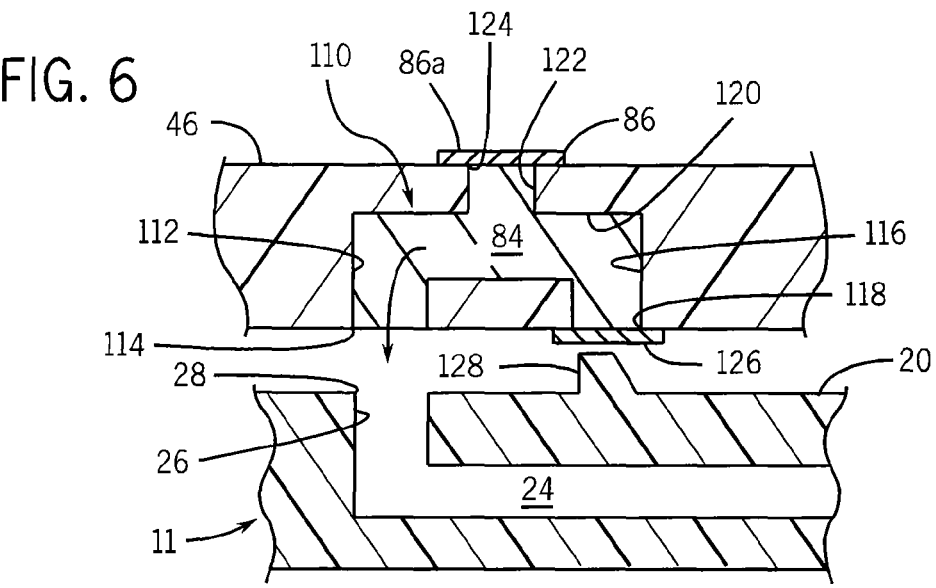
FIG. 6 is an enlarged, cross sectional view showing a further alternate embodiment of a microfluidic device for effectuating the methodology of the present invention.

Referring to FIGS. 4-6, various embodiments are depicted to urge substance 84 from first well 50 of lid 36 and into channel 24. By way of example, post 92 may project from upper surface 20 of base 11, FIG. 4. As lid 36 is positioned on base 11, it is contemplated for post 92 projecting from upper surface 20 of base 11 to be urged against non-porous membrane 82 and into first well 50. It can be appreciated that as post 92 is urged against non-porous membrane 82, substance 84 is urged from first well 50 and into channel 24 through hole 83 in non-porous membrane 82.

Alternatively, non-porous membrane 82 may be provided without hole 83 therein. As such, it is contemplated for protrusion 93 having a piercing tip 95 to project from upper surface 20 of base 11, FIG. 5. As lid 36 is positioned on base 11, piercing tip 95 of protrusion 93 projecting from upper surface 20 of base 11 engages and ruptures non-porous membrane 82. Thereafter, as protrusion 93 enters first well 50, substance 84 is urged from first well 50 and into channel 24 through: 1) the newly created hole in non-porous membrane 82; and 2) second port 52 of first well 50 of lid 36.

Once the entirety of substance 84 in first well 50 of lid 36 flows and/or is urged into channel 24, lid 36 may be removed from base 11 of microfluidic device 10 and discarded. Thereafter, additional steps of an assay may be performed by sequentially positioning additional lids 36, as heretofore described, on base 11, thereby triggering operation of microfluidic device 10.

Referring to FIG. 6, it is contemplated for first well 50 in lid 36 to be defined by channel 110 extending therethrough. Channel 110 includes a first vertical portion 112 terminating at port 114 that communicates with lower surface 48 of lid 36 of microfluidic device 10 and a second vertical portion 116 terminating at port 118 also communicating with lower surface 48 of lid 36 of microfluidic device 10. First and second vertical portions 112 and 116, respectively, of channel 110 are interconnected by and communicate with horizontal portion 120 of channel 110. Channel 110 also includes a third vertical portion 122 having a first end communicating with horizontal portion 120 of channel 110 and a second end terminating at port 124 communicating with upper surface 46 of lid 36 of microfluidic device 10.

In operation, non-porous membranes, e.g. membrane 126, are bonded to lower surface 48 of lid 36 so as to overlap ports 114 and 118 therein. First well 50 of lid 36 is loaded with a desired substance 84, such as cells and reagents, along with a cryopreservation fluid, e.g. dimethyl sulfoxide (DMSO). The cryopreservation fluid is added to substance 84 during the freezing process, hereinafter described, to prevent crystallization and cell death. Porous membrane 86 is bonded to upper surface 48 of lid 36 so as to overlap port 124 and a seal is removably bonded to outer surface 86a of porous membrane 86 and/or upper surface 46 of lid 36 to hermetically isolate the interior of first well 50, as heretofore described.

As described, substance 84 and the cryopreservation fluid in first well 50 is captured between the non-porous membranes over ports 114 and 118 and porous membrane 86. For reasons hereinafter described, it is intended for porous membrane 86 to includes micropores therein having pore sizes in a desired range, i.e., from 0.1 μm to 3 μm, so as to allow a predetermined fluid to pass therethrough, but retain substance 84 in first well 50. With substance 84 and the cryopreservation fluid captured in first well 50, substance 84 and the cryopreservation fluid may be frozen in accordance with established procedures in first well 50 of lid 36 for better packaging, storage and shipping.

In order to flow substance 84 into channel 24 through base 11 of microfluidic device 10, substance 84 must be freed from the cryopreservation fluid. By way of example, the seal is removed from lid 36 so as to expose porous membrane 86. Thereafter, lid 36 is inserted into a bath of dialysis fluid 100, e.g. cell culture media, for a time period, e.g. two to five minutes, FIG. 3. Dialysis fluid 100 diffuses through porous membrane 86 and frees substance 84 from the cryopreservation fluid. Once substance 84 is freed, as heretofore described, channel 24 is filled with a predetermined fluid and the non-porous membrane over port 114 is removed from lid 36 such that port 114 is exposed. Lid 36 is then positioned on base 11 such that: 1) lower surface 48 of lid 36 is bought into contact with or adjacent to upper surface 20 of base 11; and 2) port 114 in lid 36 is aligned with and brought into close proximity with input port 28 in base 11 such that substance 84 is in fluid communication with channel 24. In order to urge substance 84 from first well 50 of lid 36 and into channel 24, post 128 projecting from upper surface 20 of base 11 is urged against non-porous membrane 126 and into second vertical portion 116 of channel 110. It can be appreciated that as post 128 is urged against non-porous membrane 126, substance 84 is urged from channel 110 of first well 50 and into channel 24 through port 114.

As previously explained, once the entirety of substance 84 in first well 50 of lid 36 flows and/or is urged into channel 24, lid 36 may be removed from base 11 of microfluidic device 10 and discarded. Thereafter, additional steps of an assay may be performed by sequentially positioning additional lids 36, as heretofore described, on base 11, thereby triggering operation of microfluidic device 10.

Figure 7:
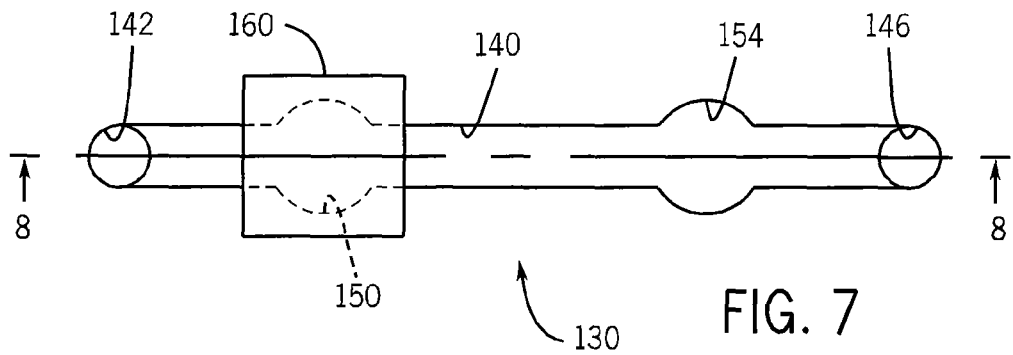
FIG. 7 is schematic, top plan view of a still further alternate embodiment of a microfluidic device for effectuating the methodology of the present invention.
Figure 8:
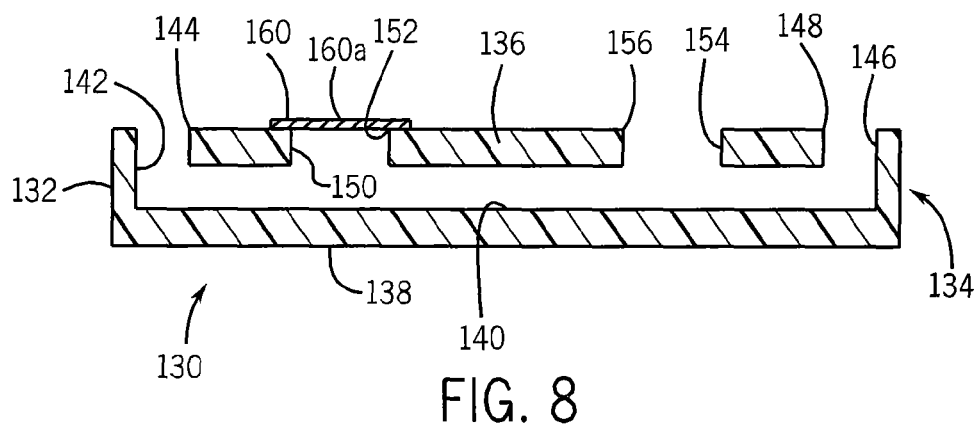
FIG. 8 is a cross-sectional view of the microfluidic device of the present invention take along line 8-8 of FIG. 7.

Referring to FIGS. 7-8, a further embodiment of a microfluidic device for performing a methodology in accordance with the present invention is generally designated by the reference numeral 130. Microfluidic device 130 may be formed from polystyrene (PS), however, other materials are contemplated as being within the scope of the present invention. In the depicted embodiment, microfluidic device 130 has first and second ends 132 and 134, respectively; and upper and lower surfaces 136 and 138, respectively. Channel 140 extends through microfluidic device 10 and includes a first vertical portion 142 terminating at an input port 144 that communicates with upper surface 136 of microfluidic device 130 and a second vertical portion 146 terminating at an output port 148 also communicating with upper surface 136 of microfluidic device 10.

Microfluidic device 130 may also include first well 150 having a first end communicating with channel 140 and a second end terminating at port 152 communicating with upper surface 136 of microfluidic device 130. Second well 154 is spaced from first well 150 and has a first end communicating with channel 140 and a second end terminating at port 156 communicating with upper surface 136 of microfluidic device 130.

In operation, first well 150 of microfluidic device 130 is loaded with a desired substance, such as cells and reagents, along with a cryopreservation fluid, e.g. dimethyl sulfoxide (DMSO). A blockage (not shown) may be providing in channel 140 to retain the desired substance and cryopreservation fluid combination in first well 150. Alternatively, the walls defining channel 140 adjacent the first end of first well 150 may include a hydrophobic pattern for prevent the desired substance and cryopreservation fluid combination from flowing through channel 140 except if a certain pressure threshold is reached. Thereafter, porous membrane 160 is bonded to upper surface 136 of microfluidic device 130 so as to overlap port 152 and a seal is removably bonded to outer surface 160a of porous membrane 160a to upper surface 136 of microfluidic device 130 to isolate the interior of first well 150, as heretofore described.

As described, the substance and the cryopreservation fluid combination is captured in first well 150 adjacent porous membrane 160. For reasons hereinafter described, it is intended for porous membrane 160 to includes micropores therein having pore sizes in a desired range, i.e., from 0.1 μm to 3 μm, so as to allow a predetermined fluid to pass therethrough, but retain the substance in first well 150. With the substance and the cryopreservation fluid combination captured in first well 150, the substance and the cryopreservation fluid combination may be frozen in accordance with established procedures in first well 150 of microfluidic device 130 for better packaging, storage and shipping.

In order to flow the substance into channel 140 of microfluidic device 130, the substance must be freed from the cryopreservation fluid. By way of example, the seal is removed from upper surface 136 of microfluidic device 10 so as to expose porous membrane 160. Thereafter, microfluidic device 130 may be inserted into a bath of dialysis fluid, e.g. cell culture media, for a time period, e.g. two to five minutes. The dialysis fluid diffuses through porous membrane 160 and frees the substance from the cryopreservation fluid.

Once the substance is freed, as heretofore described, the blockage (if present) may be removed from channel 140 and channel 140 may be filled with a predetermined fluid. In addition, a cell culture may be provided in second well 154. Fluid flow may be generated in channel 140 in any conventional matter, such as by passive pumping or by positioning an absorbent at output port 148 of channel 140. The fluid flow in channel 140 may be used to carry the substance from first well 150 into communication with the cell culture in second well 154 for processing or the like.

An additional contemplated application of the present invention is to provide a kit incorporating microfluidic device 10 wherein an end user can preload biomaterial of choice (cells, tissues, etc) in channel 24 of base 11 using a first lid 36. Thereafter, a series of additional lids may be provided in the kit for acting on the biomaterial in channel 24. For example, the series of lids may be used for a variety of purposes, such as gradient chemotaxis; to contain the biomaterial; and/or for drug treatment. After the end user manipulates the biomaterial as desired, a series of additional lids may be provided that allow the end user to complete an entire immunostaining protocol without the need for pipettes. These lids would contain liquids, including the antibodies and fluorophores, needed for detection. The end user would effectuate the protocol by applying the lids, as heretofore described, in a specified sequence. This application allows for higher throughput, cheaper costs, and faster protocol times.

It can be appreciated that lid 36 may include an array of first and second well combinations, as heretofore described. Likewise, base 11 may including an array of channels 24, as heretofore described. As a result, it is contemplated for a plurality of assays to be simultaneously conducted using a single base and lid combination, without deviating from the scope of the present invention.

Figure 9:
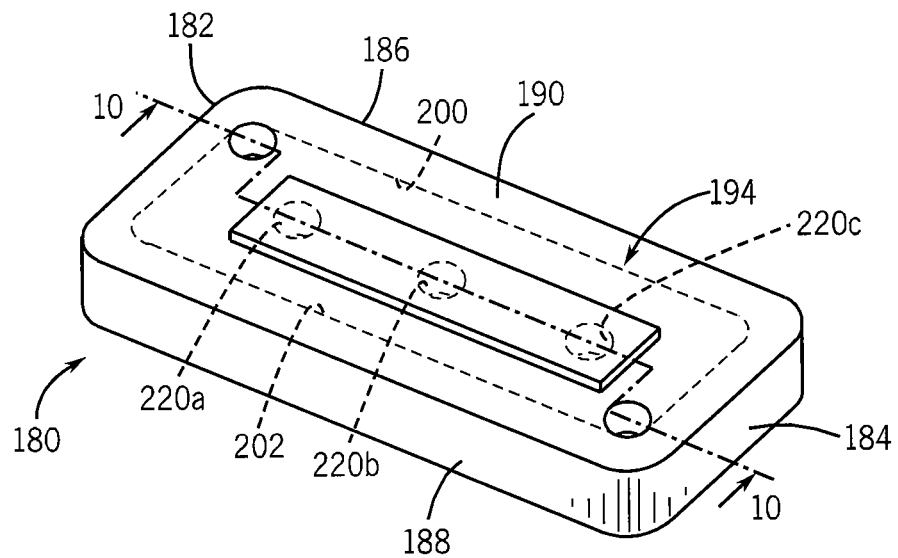
FIG. 9 is an isometric view of a still further embodiment of a lid for a microfluidic device in accordance with the present invention.
Figure 10:
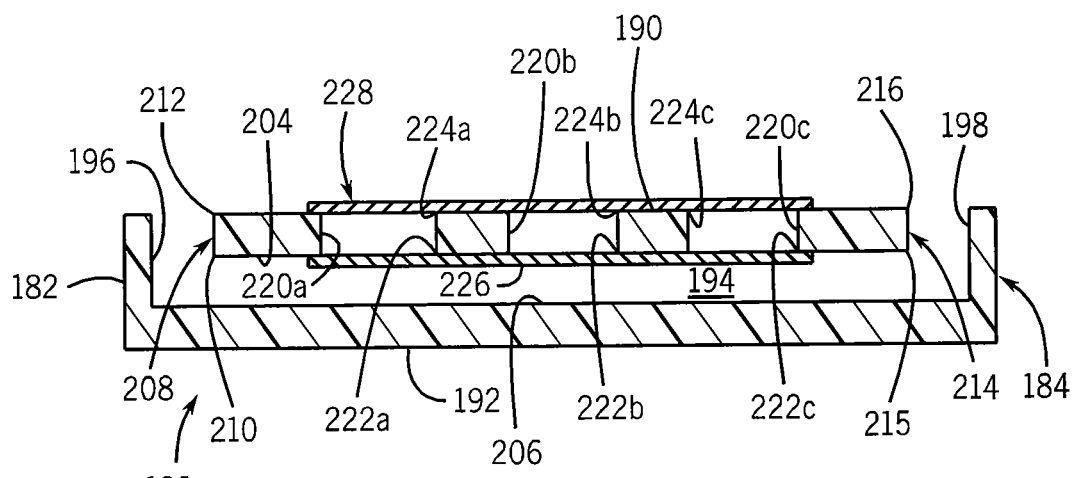
FIG. 10 is a cross sectional view of the lid of the microfluidic device of the present invention taken along line 10-10 of FIG. 9.

Referring to FIGS. 9-10, an alternate embodiment of a lid for effectuating the methodology of the present invention is generally designated by the reference numeral 180. Lid 180 is defined by first and second ends 182 and 184, respectively; first and second sides 186 and 188, respectively; and upper and lower surfaces 190 and 192, respectively. It is intended for lid 180 to be formed from polystyrene (PS), however, other materials are contemplated as being within the scope of the present invention.

Lid 180 further includes chamber 194 therein. In the depicted embodiment, chamber 194 is defined by first and second end walls 196 and 198, respectively; first and second side walls 200 and 202, respectively; and upper and lower surfaces 204 and 206, respectively. As best seen in FIG. 10, upper surface 204 is spaced from and generally parallel to upper surface 190 of lid 180 and lower surface 206 is spaced from and generally parallel to lower surface 192 of lid 180. First vertical channel 208 has a lower end 210 communicating with upper surface 204 defining chamber 194 and an upper end defining an input port 212 that communicates with upper surface 190 of lid 180. Second vertical channel 214 has a lower end 215 communicating with upper surface 204 defining chamber 194 and an upper end defining an output port 216 that communicates with upper surface 190 of lid 180.

Lid 180 also includes a plurality of axially spaced wells 220a-220c having corresponding lower ends 222a-222c communicating with chamber 194 and corresponding upper ends 224a-224c communicating with upper surface 190 of lid 180. Porous membrane 226 is bonded to upper surface 204 defining chamber 194 so as to overlap lower ends 222a-222c. For reasons hereinafter described, it is intended for porous membrane 226 to includes micropores therein having pore sizes in a desired range, i.e., from 0.1 µm to 3 µm, so as to allow a predetermined fluid to pass therethrough.

In operation, wells 220a-220c are loaded with a desired substance 84, such as cells and reagents as heretofore described, along with a cryopreservation fluid, e.g. dimethyl sulfoxide (DMSO). The cryopreservation fluid is added to substance 84 during the freezing process, hereinafter described, to prevent crystallization and cell death. Non-porous membrane 228 overlaps upper ends 224a-224c of wells 220a-220c, respectively, and is removeably bonded to upper surface 190 of lid 180 to the interior of wells 220a-220c. As described, substance 84 and the cryopreservation fluid in wells 220a-220c is captured between non-porous membrane 228 and porous membrane 226. With substance 84 and the cryopreservation fluid captured in wells 220a-220c, substance 84 and the cryopreservation fluid may be frozen in accordance with established procedures for better packaging, storage and shipping.

In order to free substance 84 from the cryopreservation fluid, dialysis fluid, e.g. cell culture media, is flowed into chamber 194 through input port 212 so as to fill chamber 194 therewith. The dialysis fluid is maintained in chamber 194 for a time period, e.g. two to five minutes. It is intended for the dialysis fluid to diffuse through porous membrane 226 and free substance 84 from the cryopreservation fluid. Once substance 84 is freed, as heretofore described, the dialysis fluid is removed from chamber 194 through output port 216. Thereafter, non-porous membrane 228 may be removed from lid 180 such that wells 220a-220c are exposed. Alternatively, non-porous membrane 228 may be pieced so as to allow substance 84 to flow therethrough. Lid 180 may be then positioned on an appropriate base, as heretofore described, such that substance 84 in wells 220a-220c are in fluid communication with channel(s) in the base. Fluid flow from wells 220a-220c may be induced in any manner, as heretofore described.

Various modes of carrying out the invention are contemplated as being within the scope of the following claims particularly pointing out and distinctly claiming the subject matter that is regarded as the invention.

We claim:

1. A lid, for a functionalized microfluidic platform, the microfluidic platform including a base having outer surface and a channel therethough for receiving fluid therein, the channel having input and output ports communicating with the outer surface, comprising:
    a body having a first well extending therethrough, the first well including first and second ports communicating therewith and being adapted for receiving a first substance therein;
    a first membrane extending over the first port of the lid, the first membrane retaining the first substance in the first well and allowing a second substance to diffuse therethrough into the first well;
    a removable seal releaseably connected to at least one of the first membrane and the body adjacent the first membrane, the seal moveable between a first position wherein the removable seal overlaps and engages the first membrane and hermetically isolates the first well and a second position wherein the removable seal is spaced from the membrane so as to allow the second substance to diffuse through the first membrane; and
    a non-porous second membrane extending over the second port, the second membrane preventing the first substance and the second substance from diffusing therethrough.

2. The lid of claim 1 wherein body includes first and second spaced surfaces, the first port communicating with the first surface and the second port communicating with the second surface.

3. The lid of claim 2 wherein the first and second surfaces are planar.

4. The lid of claim 2 wherein the first surface lies in a first plane and the second surface lies in a second plane generally parallel to the first plane.

5. The lid of claim 2 further comprising an absorbent adjacent the second surface.

6. The lid of claim 1 wherein the second membrane includes a hole therethrough.

7. The lid of claim 1 wherein the lid is movable between a first position wherein the lid is spaced from the base to a second position wherein the lid is adjacent the channel such that the first substance communicates with the input of the channel.

8. The lid of claim 6 further comprising a second seal releaseably connected to at least one of the second membrane and the body adjacent the second membrane, the second seal moveable between a first position wherein the removable seal overlaps the second membrane and isolates the first substance in the first well and a second position wherein the second seal is spaced from the body.

* * * * *